(12) United States Patent
Ho

(10) Patent No.: US 6,587,617 B2
(45) Date of Patent: Jul. 1, 2003

(54) MICRO LENS ARRAY FOR BIOASSAY

(75) Inventor: Zonh-Zen Ho, Hacienda Heights, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 8 days.

(21) Appl. No.: 09/791,092

(22) Filed: Feb. 22, 2001

(65) Prior Publication Data

US 2002/0136491 A1 Sep. 26, 2002

(51) Int. Cl.⁷ .................................................. G02B 6/28
(52) U.S. Cl. ............................. 385/25; 385/24; 385/116
(58) Field of Search ............................. 385/24–25, 116

(56) References Cited

U.S. PATENT DOCUMENTS 5,930,433 A * 7/1999 Williamson et al. ......... 385/116
6,374,024 B1 * 4/2002 Iijima .......................... 385/116

* cited by examiner

Primary Examiner—Akm E. Ullah
Assistant Examiner—Jerry T Rahll
(74) Attorney, Agent, or Firm—Lawrence S. Cohen

(57) ABSTRACT

An apparatus and method for imaging biochip spots in which a linearly spaced array of micro-lenses has a set of optical fibers which are associated with each micro-lens to receive and transmit the image magnified by the micro-lens. The micro-lenses are spaced to that of the biochip spots so that the microlens array can be positioned over a selected group of biochip spots, one for each micro-lens. The microlens array can be translated to be over selected groups of biochip spots. A detector and user devise such as a computer and a screen are used to record and view the collected images.

15 Claims, 2 Drawing Sheets

MICRO LENS ARRAY FOR BIOASSAY

FIELD OF THE INVENTION

The invention relates to imaging of biochip spots.

BACKGROUND OF THE INVENTION

One method of observing and imaging biochip spots is through the use of confocal microscopes. These devices are large and expensive.

SUMMARY OF THE INVENTION

The apparatus has a micro-lens and optical fiber array in which a plurality of micro-lenses are linearly spaced apart an amount equal to the spacing of spots on a biochip so that they can be simultaneously focused on the respective spots to enlarge the spot image. An optical fiber is terminated and fixed above each of the micro-lenses to transmit the image. A scanner will translate the array to successively adjacent groups of spots in the biochip (x direction) or if desired, along the axis of the array to an adjacent set of spots in the same line (y direction) or both. The transmitted images are sent over the optical fibers to a detector and then to a user device which may be a display screen, data processor, or other device. Confocal effect can be achieved with certain optical fiber diameters.

DETAILED DESCRIPTION

Figure 1:
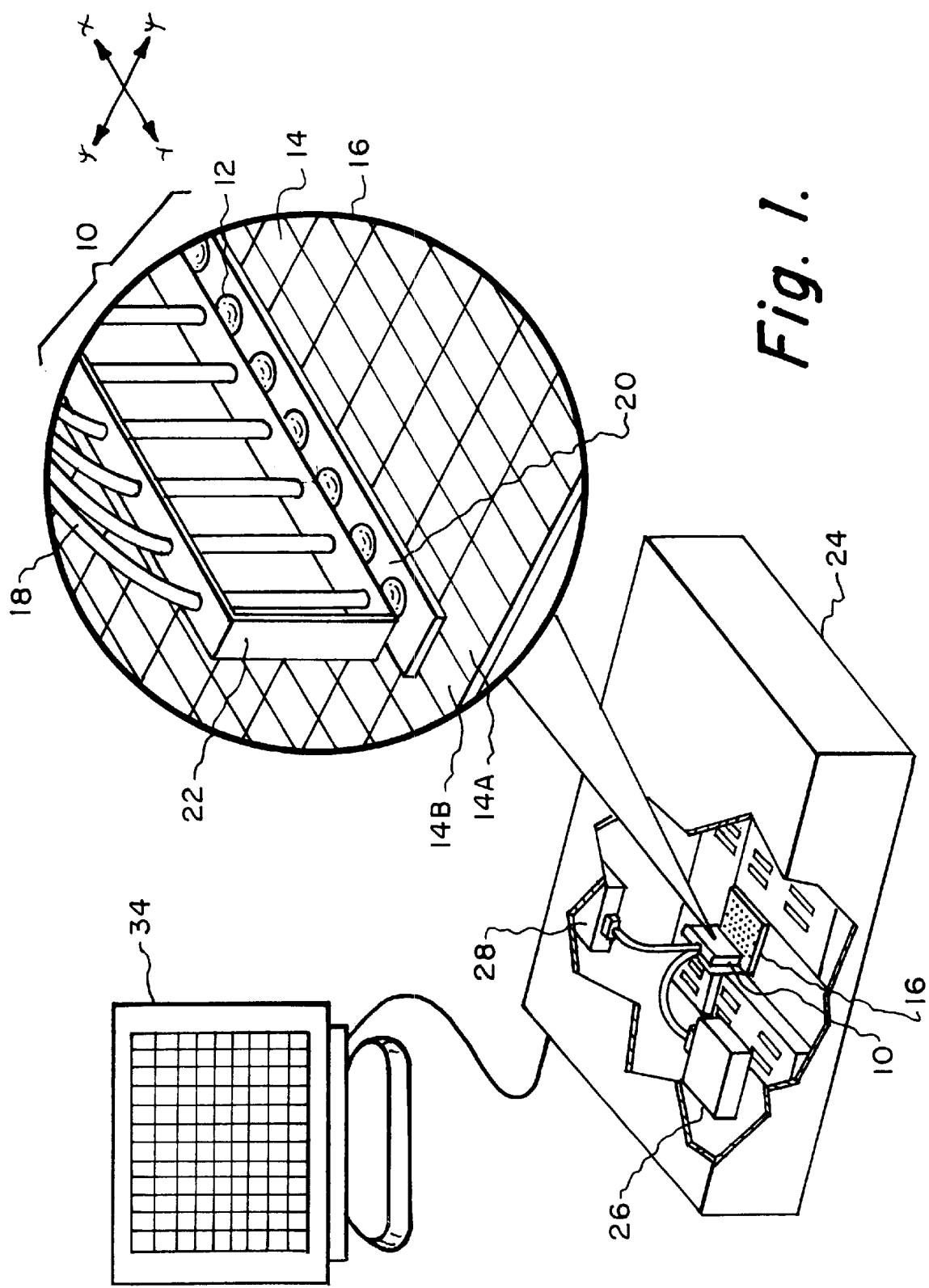
FIG. 1 shows the apparatus with an enlargement of a portion showing the micro-lens optic fiber array in place over a biochip.

As seen in FIG. 1, a micro-lens optic fiber array 10 has a plurality of micro-lenses 12 linearly arranged and spaced apart a distance equal to the spacing of the spots 14 of a biochip 16.

Mounted above the micro-lenses 12 are optical fibers 18, one for each micro-lens 12 positioned to receive the focused image transmitted through the micro-lens 12.

The micro-lenses 12 can be separate lenses, or as seen in FIG. 1, can be constructed as a multi-lens unit 20 having a spaced apart plurality of micro-lenses 12, linearly arranged and spaced to be in position over a set of linearly spaced apart spots 14 on a biochip.

A connector structure 22 is shown which terminates the optical fibers 18 so as to be securely and accurately placed to receive the magnified image transmitted through the micro-lenses 12. Structure 24 is a scanning apparatus, which enables moving the array 10 from a position over one set of spots 14A of a biochip 16, to another set of spots, 14B. The scanner can move orthogonally to the linear axis of the array 10 so as to be positioned over successively adjacent sets of spots, or it can be moved to any selected set of spots along the scanning path orthogonal to the linear axis of the array.

The scanner 24 can also be set up to move the array axially, so that, in case of a biochip that has a line of spots greater in number than the array, it can be translated along the line, that is, in the direction of the axis of the array of lenses.

Scanning of the array 10 by the scanning structure can be conveniently designated as being x direction scanning, in the direction shown by the arrows x—x parallel to the axis of the micro-lens array 10 and y direction scanning in the direction shown by the arrows y—y orthogonally to the axis of the micro-lens array.

It is preferable that the array 10 have the same number of micro-lenses and optic fiber positions as there are spots in the x direction so that only y direction scanning is necessary. Of course, as few as a single micro lens along with a single optical fiber could be implemented, which then can be translated in the x and y direction by a scanning device that moves one spot at a time, or to any selected spot on the biochip. But such an apparatus would sacrifice the advantage of having a plurality of linearly spaced micro-lenses to image an equal number of biochip spots simultaneously. Also, whatever the selected number of micro-lenses 10 in the x direction, a plurality of parallel adjacent rows of micro-lenses could be placed in a single micro-lens array.

The apparatus also has a light source 26 which is arranged to illuminate the biochip spots which are under the micro-lenses and is preferably fixed to the array 10. It can be fixed to the array 10 to move with it so as to selectively illuminate the biochips being imaged by the array.

The optical fibers 18 extend to and terminate at a detector 28 whose output is connected to either or both a recording instrument, or as shown in FIG. 1, a display screen 34 or both. In use, a biochip 16 is placed in the scanner 24 and the array 10 positioned over a selected set of spots 14. Usually the procedure will start on one side of the biochip 16 and then proceed sequentially to adjacent sets of spots 14 across the biochip 16. The apparatus can be constructed so that either the biochip 16 is moved under the array 10, or the array is moved over the biochip 16.

The microlens array of FIG. 1 may be used to test the high density biochips such as DNA chips with arrays of spots containing thousands of specific DNA binding sites. The array device is configured according to the chip configuration. An exemplary microlens array is based on the most common chip configuration, which is 100 microns by 100 microns per site and 200 microns between the centers of each site. In such an array device, using a 100-microlens linear array, 10,000 sites can be rapidly scanned in one direction of translation of the 100-microlens linear array. Based on the chip format, the proper size for the optical fibers is selected. The fibers are coupled to the microlens array as described above, each fiber having a corresponding microlens.

The microlens array will provide the necessary spot size and resolution. The spot size on the chip is determined by two factors; the numerical aperture (NA) of the objective microlens and the fiber core diameter. In an exemplary system the laser beam will be collimated with fiber coupling lens. Assuming the effective focal length (EFL) of the fiber coupling lens is $F_1$, and the EFL of the objective lens is $F_2$, then the magnification of the microlens is $M=F_1/F_2$. The estimated spot size for the fiber probe can be calculated by the following formula:

$$\text{Spot size} = (\text{fiber core diameter}) \times M + (\text{Gaussian Beam Dispersion})$$

where the Gaussian Beam Dispersion is calculated as FWHM (full-width half maximum) of the laser beam diameter. The core size of the optical fiber arranges from 3.5 microns (single mode) to 100 microns (multimode), although up to 150 microns diameter will work.

Table 1 shows combinations of different objective lens sizes and their corresponding spot size for a fiber whose core diameter is 5 microns, for example, with a 0.9 NA 1× lens, the diffraction limited spot size=1.22×λ/NA=6.9 microns. In this case the FWHM is 3.5 microns. The total estimated spot size for the fiber probe is 5 microns+3.5 microns=8.5 microns. As the table shows, the range of the spot sizes can be from 8.5 microns to 48 microns based on a fiber core diameter of 5 microns and reasonable lens choices. By carefully choosing $F_1$ and $F_2$, the spot size of the probe can be controlled so that it matches the size of biochemical spots on the biochip.

Table 1. The estimated spot size of a confocal fiber probe using a 5 micron core fiber.

| NA | EFL (μm) | CA (μm) | WD (μm) | Mag. (x) | Est. Spot Size (μm) |
|---|---|---|---|---|---|
| 0.50 | 100 | 120 | 55 | 1.0 | 8.5 |
| 0.55 | 136 | 170 | 48 | 1.4 | 10.3 |
| 0.62 | 201 | 205 | 78 | 2.0 | 13.6 |
| 0.41 | 225 | 266 | 119 | 2.3 | 14.8 |
| 0.40 | 312 | 293 | 172 | 3.1 | 19.1 |

Figure 2:
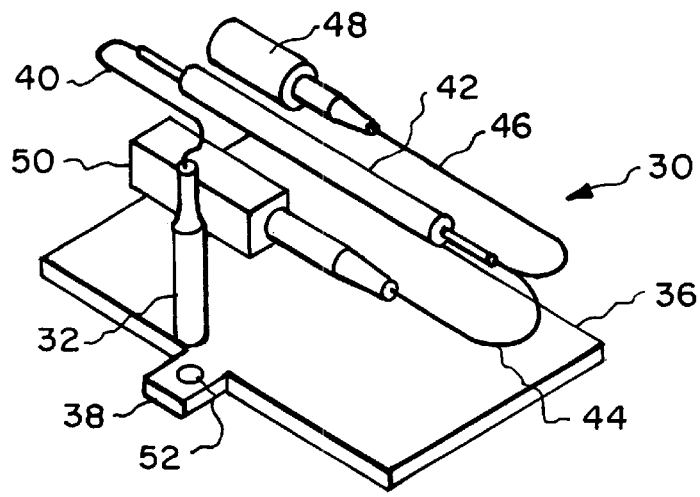
FIG. 2 shows a test bench set up for testing the concept of the invention.

FIG. 2 is a test bench set-up 30 used to confirm confocal operation of the microlens array. This set-up 30 has a battery back and driver which are not shown. A sensor head assembly 32 contains the micro-lens and optical fiber assembly 34 which is shown in detail in FIG. 3. A fiber sensor base plate 36 supports the set-up and has a test specimen area 38. Optical fiber 40 extends from the sensor head assembly 32 to one end of a fused fiber coupler 42. Exiting the fused fiber coupler 42 are optical fibers 44 and 46. Optical fiber 46 goes to a laser 48 and the optical fiber 44 goes to a filter detector 50. The laser 48 is a compact diode laser (635 nm, 30 mW) pigtailed to the single mode fiber 46 to provide light source for illumination which was operated with a 9 VDC battery. The output beam of the fiber is collimated. The lens in the sensor head assembly 32 is an aspheric microlens (numerical aperture (NA)=0.62, effective focal length (EFL)=2 mm, CT=2.0 mm from Geltech of Florida to generate a minimal spot size of 10 microns. The bifurcated fiber delivered light to the sample 52 and directed the fluorescence light back to a compact PMT/high gain amplifier and color filter 50. The combination of the optical fiber "pinhole" and the high NA microlens offers a sharp, high contrast fluorescence image.

Figure 3:
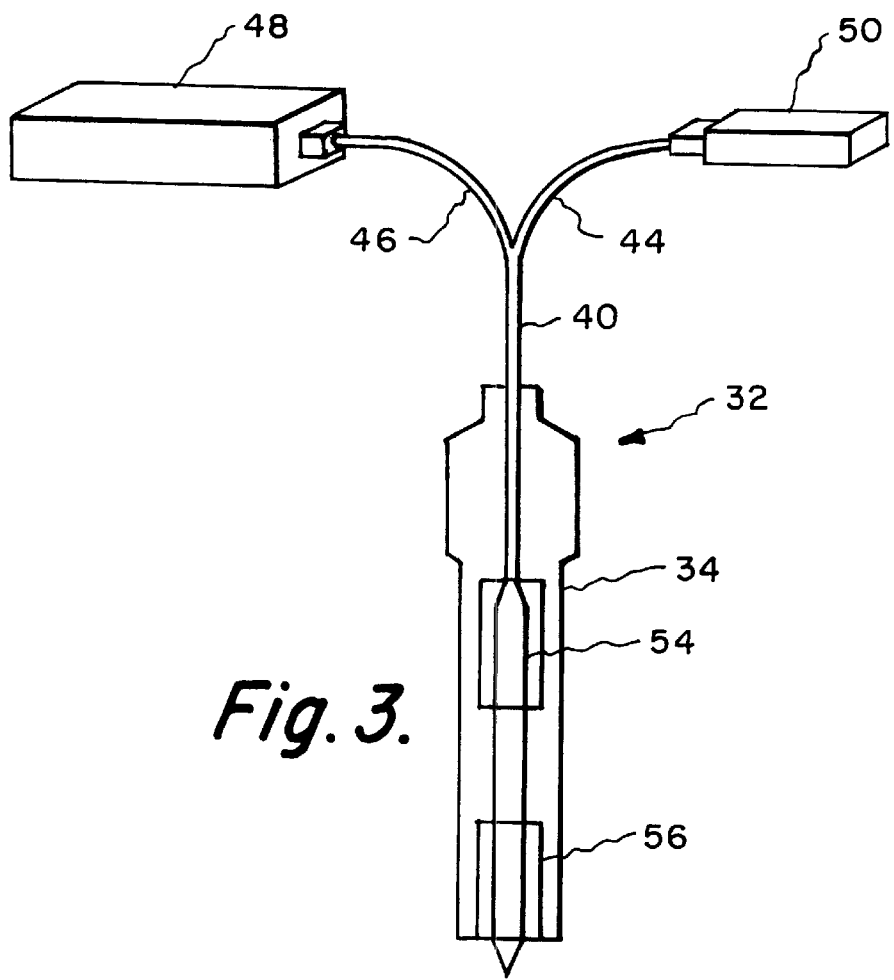
FIG. 3 shows a micro-lens construction according to the invention.

FIG. 3 shows schematically, detail of the sensor head assembly 32, having aligned micro-lenses 54 and 56, bifurcated optical fiber 40 terminating at and optically aligned with the micro-lens 54. The bifurcated optical fiber 40 goes via branch 46 to the laser 48 and the other branch 44 to a filter detector 50.

An operational test of the test bench set-up 30 as described above was conducted. The fiber used was a 3.5 micron core single mode fiber. The test specimen was a CY5 dye on a glass slide. The specimen was diluted with water to a solution concentration of 1 mg/ml. The spot was about 2 mm in diameter. The laser diode and the PMT were turned on. The PMT was calibrated. The background signal was measured. The sample was placed under the lens. An increase in signal was observed. Confocal effect was observed. In the test, the z axis (vertical distance to the spot) was adjusted, up and down, in increments of ½ mm. The signal was observed to diminish when adjusted off the calibration point for which the confocal effect was observed. The optical signal is collected by the PMT, converted to voltage and read through a voltmeter.

Numerous modifications and alterations can be made to the apparatus and processes of the invention without departing from its scope as defined in the following claims and it is intended that the claims cover such modifications and alterations as may permissibly fall within their scope and equivalents thereof.

What is claimed is:

1. A fiber optic apparatus for use with a biochip having an array of spots comprising;

a micro-lens optical fiber array having a plurality of micro-lenses arranged linearly and spaced apart by a distance equal to the spacing of the spots on the biochip so that when set in a position above the spots each micro-lens will be focused on one of the spots and having a plurality of optical fibers each positioned above one of the micro-lenses to receive the image, passed through the micro-lens, of the respective biochip spot wherein the microlenses, the optical fiber core size, and distance between the optical fiber and the microlens are selected to provide confocal effect;

a scanning apparatus to which the micro-lens optical fiber array is attached having a mechanism for selectably translating said array from a position over one set of biochip spots to a position over another set of biochip spots.

2. The apparatus of claim 1 for use with a biochip array having spot spacing sizes in the range from 10 um to 100 um, the spacing of the micro-lens optical fiber array being in the range from 10 um to 100 um and matching the spot spacing of the biochip.

3. The apparatus of claim 1 wherein the micro-lens array comprises a holding structure having a first portion in which the spaced part micro-lenses are fitted and a second portion in which the optical fibers are fitted.

4. The apparatus of claim 1 further comprising a detector having a connection to which the optical fibers are attached.

5. The apparatus of claim 4 further comprising a display screen attached to an output of the detector for viewing the biochip spots which are under the micro-lens.

6. The apparatus of claim 4 further comprising a camera for recording the images of the spots under the microlenses.

7. The apparatus of claim 4 further comprising a recording means to record the images of the spots under the microlenses.

8. The apparatus of claim 1 further comprising a light source positioned to illuminate the spots of a biochip which are below the micro-lenses.

9. The apparatus of claim 1 wherein the plurality of optical fibers have a core of up to about 150 microns.

10. The apparatus of claim 9 wherein the plurality of optical fibers have a specified core size of 3.5 microns to about 5 microns.

11. The apparatus of claim 1 wherein the optical fiber array further comprises a second microlens aligned with and spaced from each of said microlens and proximate each optical fiber.

12. The apparatus of claim 1 wherein at least one light source is provided and light from the at least one light source is directed into each optical fiber to illuminate the biochip spot under the respective microlenses.

13. The apparatus of claim 12 wherein the optical fiber has a bifurcated fiber coupler defining one optical fiber branch extending to receive light from the at least one light source to illuminate the biochip spot and another optical fiber branch extending to carry the reflected image to a detector.

14. The apparatus of claim 12 wherein the at least one light source is a laser light source.

15. A method for imaging biochip spots or portions thereof comprising;

providing a microlens optical fiber array having a plurality of micro-lenses arranged linearly and spaced apart by a distance equal to the spacing of the spots on the biochip so that when set in a position above the spots each micro-lens will be focused on one of the spots and having a plurality of optical fibers each positioned above one of the micro-lenses to receive the image, passed through the micro-lens, of the respective biochip spot wherein the microlenses, the optical fiber core size, and distance between the optical fiber and the microlens are selected to provide confocal effect;

placing the microlens optical fiber array over a first selected group of spots;

recording the images of the first selected group of spots;

translating the microlens optical fiber array to a position over one or more subsequently selected group of spots;

recording each of the images of each of the one or more subsequently selected group of spots.

* * * * *